United States Patent [19]

Blaszkiewicz et al.

[11] Patent Number: 5,073,362

[45] Date of Patent: Dec. 17, 1991

[54] DICARBOXYLIC ACID-BIS(3,5-DICARBAMOYL-2,4,6-TRIIODOANILIDES) AND X-RAY CONTRAST MEDIA CONTAINING THEM

[75] Inventors: Peter Blaszkiewicz; Ulrich Speck, both of Berlin, Fed. Rep. of Germany

[73] Assignee: Schering Aktiengesellschaft, Berlin and Bergkamen, Fed. Rep. of Germany

[21] Appl. No.: 554,948

[22] Filed: Jul. 16, 1990

Related U.S. Application Data

[63] Continuation of Ser. No. 245,242, Sep. 16, 1988, abandoned.

[30] Foreign Application Priority Data

Sep. 17, 1987 [DE] Fed. Rep. of Germany ....... 3731542

[51] Int. Cl.$^5$ ................ A61K 49/04; C07C 237/46
[52] U.S. Cl. ........................................ 424/5; 564/153
[58] Field of Search ........................... 564/153; 424/5

[56] References Cited

U.S. PATENT DOCUMENTS

| 4,239,747 | 12/1980 | Pfeiffer et al. | 424/5 |
| 4,341,756 | 7/1982 | Sovak et al. | 424/5 |
| 4,364,921 | 12/1982 | Speck et al. | 424/5 |
| 4,439,613 | 5/1984 | Sovak et al. | 549/347 |

FOREIGN PATENT DOCUMENTS

| 0108638 | 5/1684 | European Pat. Off. . |
| 0023992 | 2/1881 | European Pat. Off. . |
| 0049745 | 4/1982 | European Pat. Off. . |
| 2628517 | 1/1978 | Fed. Rep. of Germany . |
| 2805928 | 10/1978 | Fed. Rep. of Germany . |

Primary Examiner—Jose G. Dees
Assistant Examiner—Vera C. Clarke
Attorney, Agent, or Firm—Millen, White & Zelano

[57] ABSTRACT

Dicarboxylic acid bis-(3,5-dicarbomoyl-2,4,6-triiodoanilides) of general formula I

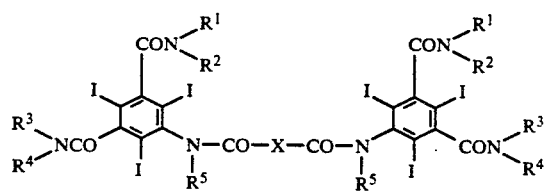

wherein the amide radicals —$CONR^1R^2$ and —$CONR^3R^4$ are different from one another and $R^1$ is a hydrogen, a lower alkyl radical or $R^2$, $R^2$ is a straight-chain or branched-chain monohydroxy or polyhydroxy alkyl radical, $R^3$ is hydrogen, a lower alkyl radical or $R^4$, $R^4$ is a straight-chain or branched-chain monohydroxy or polyhydroxy alkyl radical, $R^5$ is hydrogen, a lower alkyl radical or a monohydroxy or polyhydroxy alkyl radical, X is a straight-chain or branched-chain alkylene with 1 to 6 carbon atoms, which optionally can be substituted by 1 to 6 hydroxy or alkoxy groups or interrupted by one or more oxygen atoms, possess good pharmacological and physicochemical properties rendering them outstandingly suitable as radiopaque substances in X-ray contrast media for use in all fields of application for X-ray contrast media.

20 Claims, No Drawings

DICARBOXYLIC ACID-BIS(3,5-DICARBAMOYL-2,4,6-TRIIODOANILIDES) AND X-RAY CONTRAST MEDIA CONTAINING THEM

This application is a continuation of application Ser. No. 245,242, filed Sept. 16, 1988, now abandoned.

BACKGROUND OF THE INVENTION

X-ray contrast media are indispensable auxiliary agents in the diagnosis of numerous diseases, as, for example, arteriosclerotic vascular processes, tumors, infarcts, diseases of the kidneys and efferent urinary passages. Since the introduction of the first products great advances have been made.

For example, the chemotoxic properties of the contrast media have been greatly reduced. For clinical use this means a smaller occurrence of side effects such as nausea, vomiting, certain circulatory reactions, urticaria, bronchospasm and other symptoms up to shock and death. Chemotoxic effects, e.g., as $LD_{50}$, are pharmacologically measurable after intravenous injection.

The products used earlier were very greatly hypertonic (e.g., up to 8 times the osmolality of blood) and consequently caused a great number of potentially serious side effects such as, e.g., drop in blood pressure, bradycardia up to cardiac arrest, disturbances of the blood-brain barrier, intense pain, etc. Newer contrast media exhibit only 2 to 3 times the osmolality of blood in the clinically customary concentrations.

Although both the chemotoxicity and the hypertonicity of the contrast media have been reduced, so far no ideal values could be achieved.

Even the latest so-called nonionic contrast media still caused serious and very serious incidents (McClennan, Radiology 162, 1:1-8 [1987]: "Low-osmolality contrast media: Premises and Promises"), which have to be ascribed to chemical-toxic actions.

Also the osmolality of these products is still much too high to be able to speak of physiological contrast media. Therefore it is not surprising that at least a certain percent of patients complain about the intense pain during the examination with these products. ("Pain and hemodynamic effects in aortofemoral angiography" in Acta Radiol. Diagnosis 23, 4: 389-399 [1982].)

From experience these problems can be solved to a large extent by synthesis of water-soluble, very hydrophilic "nonionic dimers," i.e., of contrast media molecules, which consist of the linkage of two triiodinated aromatic substances. Such substances were first described in DOS 26 28 517. Since then a series of very similar structures has been described, e.g., in DOS 28 05 928, EP 0023992, EP 0049745 and EP 0108638.

Nonionic dimers are generally not hypertonic in comparison with the body fluids in all the concentrations customary for X-ray diagnosis. Further, some representatives of this substance class exhibit only very slight chemotoxicity, i.e., extremely high $LD_{50}$ values are achieved after intravenous injection.

Despite these advantages, contrast media based on nonionic dimers thus far have hardly had any clinical use. The reason for this is the problem of high viscosity. This is a factor especially for highly concentrated solutions, which are necessary for certain especially critical angiographic examinations. Thus, angiographic examinations of the coronary vessels and ventricles are to be selectively performed only with contrast media solutions which contain 350 mg or more of iodine/ml.

In this case the contrast media solutions must be injected with very high speed through about 100 cm of long very narrow catheters. Solutions with over 12 to 15 cp at 37° C. are no longer suitable for the purpose. In addition, very fast intravenous injection, as is necessary for various modern X-ray techniques, very well tolerated and slightly viscous contrast media are necessary.

The viscosity of the nonionic dimer contrast media depends on a series of factors, of which the iodine content of the molecules plays an essential role. With an increasing iodine content the viscosity of the solutions of the respective molecules decreases, but at the same time so does their solubility in water.

SUMMARY OF THE INVENTION

The invention relates to new dicarboxylic acid-bis-(3,5-dicarbamoyl-2,4,6-triiodoanilides) of general formula I

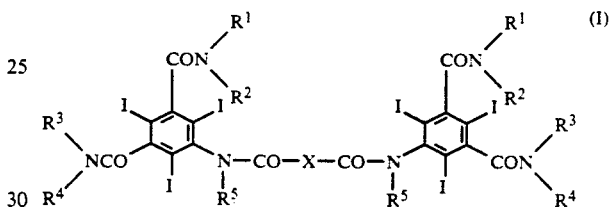

in which the amide radicals $-CONR^1R^2$ and $-CONR^3R^4$ are different from one another and $R^1$ means a hydrogen atom, a lower alkyl radical or $R^2$, wherein $R^1$ and $R^2$ may be the same or different, $R^2$ means a straight-chain or branched-chain monohydroxy or polyhydroxy alkyl radical, $R^3$ means a hydrogen atom, a lower alkyl radical or $R^4$, wherein $R^3$ and $R^4$ may be the same or different, $R^4$ means straight-chain or branched-chain monohydroxy or polyhydroxy alkyl radical, $R^5$ means a hydrogen atom, a lower alkyl radical or a monohydroxy or polyhydroxy alkyl radical, and X means a straight-chain or branched-chain alkylene with 1 to 6 carbon atoms, which optionally can be substituted by 1 to 6 hydroxy or alkoxy groups or interrupted by one or more oxygen atoms, a process for the production of these compounds, X-ray contrast media containing compounds of formula I as the radiopaque substance, and a method of performing X-ray imaging using the X-ray contract media, e.g., rendering radiopaque a hollow or fluid-filled body part.

Radicals $R^1$ and $R^3$ independently are lower alkyl radicals, preferably straight-chain radicals with 1 to 4 carbon atoms, preferably with 1 to 2 carbon atoms as, for example, ethyl, propyl, butyl, especially methyl.

Radicals $R^2$ and $R^4$ independently are straight-chain or branched-chain monohydroxy or polyhydroxy alkyl radicals with 2 to 8 carbon atoms, preferably 2 to 5 carbon atoms. Straight-chain radicals $R^2$ and $R^4$ have most preferably 2 to 4 carbon atoms and branched-chain radicals have most preferably 3 to 5 carbon atoms. The hydroxy groups in radicals $R^2$ and $R^4$ can be present as primary or secondary hydroxy groups. Radicals $R^2$ and $R^4$ usually contain 1 to 5 hydroxy groups, preferably 1 to 3 hydroxy groups. As radicals $R^2$ and $R^4$ there can be mentioned, for example:

2-hydroxyethyl, 2-hydroxypropyl, 3-hydroxypropyl, 2,3-dihydroxypropyl, 1-hydroxymethyl-2-hydroxyethyl, 2,3-dihydroxybutyl, 2,4-dihydroxybutyl, 3,4-dihydroxybutyl, 3-hydroxy-2-(hydroxymethyl)-propyl, 2,3-dihydroxy-1-methylpropyl, 2-hydroxy-3-(hydroxymethyl)-butyl, 2,3,4-trihydroxy-butyl, 2,4-dihydroxy-3-(hydroxymethyl)-butyl, 3-hydroxy-2,2-bis-(hydroxymethyl)-propyl, 4-hydroxy-3,3-bis-(hydroxymethyl)-butyl, 4-hydroxy-2,2-bis-(hydroxymethyl)-butyl, 2-hydroxy-1,1-bis-(hydroxymethyl)-ethyl, 1,3-dihydroxy-isopropyl and 2,3-dihydroxy-1-hydroxymethylpropyl, etc.

Radical $R^5$ usually is a lower alkyl radical preferably straight-chain alkyl radicals with 1 to 4, preferably with 1 to 2, carbon atoms as, for example, the ethyl, propyl or butyl, especially the methyl radical. When $R^5$ represents a monohydroxy or polyhydroxy alkyl radical, it has 2 to 6, preferably 2 to 4, carbon atoms and is substituted with 1 to 5, preferably 1 to 3, hydroxy groups. Suitable radicals include, for example, 2-hydroxyethyl, 2,3-dihydroxypropyl, etc.

X, as a straight-chain or branched-chain divalent alkylene bridging group, which can be interrupted by one or more oxygen atoms, usually contains 1 to 6 carbon atoms. Preferably it is a straight-chain alkylene with 1 to 4 carbon atoms, which can be interrupted by one or more, preferably one, two or even three oxygen atoms.

Suitable examples are, e.g., —$CH_2$—, —$(CH_2)_4$—, —$(CH_2$—$CH_2$—O—$CH_2$—$CH_2)_2$— and —$(CH_2$—O—$CH_2)_3$—. As branched-chain radicals X there are suitable: —$CHCH_3$, —$[CH_2C$—$(CH_3)_2$—$CH_2]$—, —$[CH_2$—$CH(CH_3)$—$CH_2CH_2]$— and the like. X, as straight-chain or branched-chain alkylene, can also be substituted by hydroxy or alkoxy groups, e.g., of 1-7 C-atoms. Thus each carbon atom of X can contain a hydroxy or alkoxy group.

As examples there can be mentioned

Radical X can also be substituted by hydroxyalkyloxy groups, e.g., of 1-7 C atoms, as for example

In X, the alkoxy portions include the group benzyloxy and preferably is $C_{1-4}$-alkoxy.

DETAILED DISCUSSION

It was found, surprisingly, that aqueous solutions of the compounds of formula I according to the invention have excellent compatibility and blood isotonia. In addition, they have, even at concentrations of 300 to 400 mg of iodine/ml, the desired sufficiently low viscosity to make possible a universal application in angiography both for the fast addition mode and in the application of highly concentrated solutions through narrow catheters.

The compounds according to the invention of general formula I thus are outstandingly suitable as radiopaque substances for production of or for use in X-ray contrast media. The new compounds have all the properties which are required of X-ray contrast media. Many, although nonionic, are very easily water-soluble. The new compounds represent outstandingly compatible X-ray contrast media, which are suitable in angiography, urography, myelography, lymphography and for representing various body cavities and for other radiological examinations.

Because of their faint and neutral taste some of the compounds are outstandingly suitable for oral application and for introduction into the lung. The bitter and nauseating taste inherent in the usual contrast media is a serious drawback especially in gastrography and bronchography.

The invention thus also relates to new X-ray contrast media based on the compounds of general formula I. Production of the new X-ray contrast media takes place in a way known in the art, e.g., in that the radiopaque substance is put in a form suitable for intravenous application with the additives usual in galenicals, e.g., stabilizers such as sodium edetate, calcium disodium edetate, physiologically compatible buffers, sodium chloride, etc. The concentration of the new X-ray contrast media in the aqueous medium fully conforms with the conventional X-ray diagnostic method. The preferred concentrations and dosages of the new compounds are in the ranges of 50-500 mg I/ml for the concentration and 5-500 ml for the dosage. Concentrations between 100 and 400 mg I/ml are especially preferred.

The invention further relates to a process for the production of the compounds of general formula I, which is characterized in that in a way known in the art a dicarboxylic acid-bis(3-carbamoyl)-(5-chlorocarbonyl)-2,4,6-triiodoanilide) of general formula II

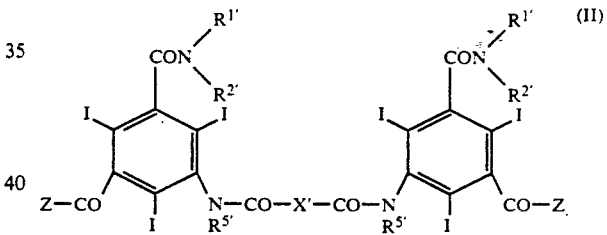

in which $R^{1'}$ and $R^{2'}$ have the meaning of $R^1$ and $R^2$, and the free hydroxyl groups present in $R^1$ and $R^2$ optionally can be present in protected form, X' has the meaning of X or of a substituent to be converted into X, $R^{5'}$ has the meaning of a hydrogen atom or a lower alkyl radical and Z means a reactive oxygen radical or ester radical, is reacted with a base of formula III

in which $R^{3'}$ and $R^{4'}$ have the meaning of $R^3$ and $R^4$, and free hydroxyl groups present in $R^3$ and $R^4$ optionally can be present in protected form and then optionally the aromatic acylamino groups are N-alkylated, namely in case the compounds of general formula I are desired with $R^5$ equal to lower alkyl radical, are reacted with a compound of general formula IV

and in case the compounds of general formula I with $R^5$ equal to monohydroxyl or polyhydroxyl alkyl radical are desired, are reacted with a compound of general formula V

in which $R^5$ represents a lower alkyl group,

A represents a hydrogen atom or a monohydroxy or polyhydroxy alkyl radical with 1 to 4 carbon atoms and 1 to 4 hydroxyl groups, B and D together either form an oxido ring or B represents a hydroxy group and D represents a chlorine or bromine atom or a sulfate group or alkylsulfate group, and in case group X of compound I means a methylene group and all hydroxyl groups present in compound I are present in protected form, optionally is reacted with a suitable hydroxylating agent and/or the protecting groups of protected hydroxy groups are removed.

For the amidizing reaction of the compound of formula II hydroxyl groups present in groups $R^{1'}$, $R^{2'}$ and $X'$ can be present in free or protected form. If these hydroxyl groups are to be present in protected form, all hydroxyl protecting groups are suitable, which are, of course, suitable for an intermediate hydroxyl group protection, i.e., which can easily be introduced and, with re-formation of the ultimately desired free hydroxyl group, can also be easily cleaved off again. Protection by esterification is preferred, e.g., by introduction of the benzoyl or acyl, especially of the acetyl radical. Suitable protecting groups are also ether groups such as, for example, benzyl, di- and triphenyl methyl ether groups as well as acetal and ketal groups with, e.g., acetaldehyde and acetone.

Amidation of the two carboxyl groups, which are present as reactive acid radical or ester radical Z, takes place in a suitable solvent at 0° C. to 120° C., preferably at 20° C. to 100° C. Suitable solvents are, inter alia, polar solvents such as, for example, water, dioxane, tetrahydrofuran, dimethylformamide, dimethylacetamide, hexametapol, acetone and the like and their mixtures. Since in the amidation reaction per reacted molecule of the compound of formula II two moles of acid (from the reactive acid radical or ester radical) are freed, which must be neutralized, for each reactive acid group or ester group two equivalents of base are required, suitably in excess of at least 10%. For practical implementation, the dissolved or suspended starting material of formula II is reacted with at least 4.4 equivalents of the base of formula III or with at least 2.2 equivalents of the base of formula III and additionally with at least 2.2 equivalents of a different base of formula III, which then acts as a proton acceptor. Tertiary amines are advantageously used as proton acceptors, such as, for example, triethylamine, tributylamine, pyridine or dimethylaminopyridine or inorganic bases such as, for example, sodium bicarbonate, sodium carbonate or the corresponding potassium salts and their hydrates. The inorganic and organic salts resulting in the course of the reaction are separated in a known way, e.g., by use of ion-exchangers or by filtration over known adsorbents such as, for example, diaion or Amberlite ® XAD-2 and 4.

The optionally subsequent N-alkylation of the aromatic acylamino groups to compounds of formula I, in which $R^5$ means a lower alkyl radical or a monohydroxy or polyhydroxy alkyl radical, also takes place according to methods known to one skilled in the art, e.g., in polar solvents such as alkanols or alkanediols such as methanol, ethanol or propanediol or in polyethers such as ethylene glycol diethyl ether, diethylene glycol dimethyl ether, etc., or their mixtures in the presence of strong bases, such as alcoholates of sodium, potassium or their hydrides.

In case $R^5$ means a lower alkyl, compounds of general formula IV ($R^5$-D) are used as alkylation agents such as, e.g., alkyl halides or sulfates or their equivalents such as methyl iodide, methyl bromide or dimethyl sulfate for compounds of formula I with $R^5$=methyl or ethyl bromide, ethyl iodide or diethyl sulfate for compounds of formula I with $R^5$=ethyl. For the production of the compounds of formula I with $R^5$ meaning a monohydroxy or polyhydroxy alkyl radical alkylation reagents of general formula V

are used, in which

A represents a hydrogen atom or a $CH_2OH$ group and

B and D together either mean the oxygen atom of an oxido ring or

B represents a hydroxy group and

D represents a chlorine or bromine atom or a sulfate or alkyl sulfate group, such as, for example, chloroethanol, alkylene oxide, chloropropanediol-(2,3) or 2,3-oxidopropanol at a temperature from room temperature to 80° C., preferably at 20° C. to 60° C. Alkylation reagent and alcoholates in this case are used in excess. For working-up, after cooling to room temperature it is worked up in the usual way and desalted by ion-exchanger.

Another possibility for the alkylation consists in that compound I, with $R^5$ meaning a hydrogen atom, is put into reaction with intermediately protected hydroxy groups. This takes place, as already described for the amidation, according to usual methods by introduction of easily recleavable groups, for example, by etherification (e.g., introduction of the triphenyl methyl radical).

The hydroxyl group protection can be achieved by ketalation or acetalation, e.g., by means of acetaldehyde, acetone, 2,2-dimethoxypropane or dihydropyran.

The later cleavage of the intermediately introduced protecting groups with release of the ultimately desired hydroxyl groups also takes place according to methods as already described (see above).

For the production of the compounds according to the invention of formula I with X meaning hydroxy methylene, it also is possible, if desired, in a hydrolyzing manner to oxidize the compound of formula I, in which X represents the methylene group and all existing hydroxyl groups are present in protected form, with a suitable reagent such as, for example, lead tetraacetate or lead tetrabenzoate, and inert solvents such as dioxane, anhydrous acetic acid or propionic acid are used and the reaction is performed at 60° C. to 100° C., preferably at 80° C. to 100° C. Then—if desired—the hydroxy protecting groups are again cleaved off. It is also possible to convert a halogen- substituent contained in X' into a hydroxy group in a way known in the art, e.g., by the action of alkali or silver salts of lower carboxylic acids in polar solvents at temperatures between 20° and 120° C.

Starting compounds which can be used for the synthesis of compounds of general formula II can be produced according to processes known in the art, for example, from 5-nitroisophthalic acid monoethyl ester, as the following production instructions explain in greater detail. The conversion of these to the compounds of Formula II is also conventional. See, e.g., U.S. Pat. No. 4,364,921, U.S. Pat. No. 4,341,756, U.S. Pat. No. 4,439,613 and U.S. Pat. No. 4,239,747.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application, West Germany P. 37 31 542.0, filed Sept. 17, 1987, are hereby incorporated by reference.

EXAMPLES

Production of 5-amino-2,4,6-triiodoisophthalic acid-(2,3-diacetoxy-propyl) amide chloride a) 5-Nitroisophthalic acid-mono-(2,3-dihydroxy-propyl) amide 239 g (1 mol) of 5-nitroisophthalic acid monoethyl ester and 200.4 g (2.3 mol) of aminopropanediol-2,3 are stirred for 2 hours at about 200 mm of mercury and 95° C. and the resulting ethanol is distilled off in the process. A clear melt results from the suspension first present. After the indicated time the reaction is complete. The melt is dissolved in 1 liter of water, the solution is stirred for 30 minutes at 60° C. with 24 g of activated carbon, filtered and the filtrate is acidified with concentrated hydrochloric acid to pH 1 and inoculated with authentic material. At room temperature the product crystallized out abundantly within 15 hours. It is suctioned off, washed with 250 ml of water and dried in a vacuum at 50° C. The yield is 260 g (0.914 mol)=91.4% of theory.

b) 5-Amino-2,4,6-triiodoisophthalic acid-mono-(2,3-dihydroxy-propyl) amide 284.2 g (1 mol) of 5-nitroisophthalic acid mono-(2,3-dihydroxy-propyl) amide is dissolved in 1 liter of water by addition of 100 mg of 33% aqueous ammonia, 4 g of 20% palladium calcium carbonate is added and the solution or suspension is hydrogenated in a 5-liter autoclave within one hour to the corresponding amino compound. The hydrogen pressure is 40 bars at the beginning, 6 bars at the end. In the meantime the temperature rises to 45° C. The catalyst is filtered off and the filtrate, in which the intermediate product 5-amino-isophthalic acid mono-(2,3-dihydroxy-propyl) amide is dissolved, it put into the iodination reaction. For this purpose, the solution is acidified with 150 ml of concentrated hydrochloric acid, warmed to 80° C. and mixed within one hour with 1 liter (4 mol) of 4N $NaICl_2$ solution. After the addition is completed, it is kept for 3 more hours at this temperature, the heating is then cut off and is stirred for another 10 hours. In this time the product crystallizes out. It is suctioned off, suspended in 1 liter of water, mixed with $Na_2S_2O_5$ until negative reaction of potassium iodide/starch paper, the crystallizate is suctioned off, suspended in 2 liters of water, dissolved by addition of 32% sodium hydroxide solution, stirred with 60 g of activated carbon for 1 hour at 50 to 60° C., filtered, acidified with concentrated hydrochloric acid and again crystallized. The crystallizate is suctioned off after 10 hours and dried in a vacuum at 50° C. The yield is 486.6 g (0.77 mol)=77% of theory relative to the nitro compound used.

c) 5-Amino-2,4,6-triiodoisophthalic acid mono-(2,3-diacetoxy-propyl) amide 300 g (0.475 mol) of 5-amino-2,4,6-triiodoisophthalic acid mono-(2,3-dihydroxy-propyl) amide is suspended in 1.4 liter of ethyl acetate, mixed with 178.07 g (1.74 mol) of acetic anhydride and 5.7 g (47.5 mmol) of 4-dimethylaminopyridine and the mixture is heated to boiling. The suspension changes into a solution from which the product quickly crystallizes out in the boiling heat. The acetylation is completed after 1 hour. The excess acetic anhydride is reacted to ethyl acetate by addition of ethanol, cooled to room temperature, the crystallizate is suctioned off, washed with ethyl acetate and dried in a vacuum at 50° C. The yield is 300.2 g (0.42 mol)=88.4% of theory.

d) 5-Amino-2,4,6-triiodoisophthalic acid-(2,3-diacetoxy-propyl)-monoamide chloride 320 g (0.45 mol) of 5-amino-2,4,6-triiodoisophthalic acid-mono-(2,3-diacetoxy-propyl) amide is suspended in 1 liter of 1,2-dichloroethane, 107.1 g (0.9 mol) of thionyl chloride is added and heated to boiling temperature. After about 30 minutes, a clear solution is present, after 50 minutes the reaction is complete. It is cooled to room temperature, stirred with 5 liters of 5% sodium bicarbonate solution for 15 minutes, the phases are separated, the organic phase concentrated by evaporation. 315 g (0.43 mol)=95.6% of theory of amorphous product is obtained.

Production of 5-amino-2,4,6-triiodoisophthalic acid (2-acetoxy-ethyl) monoamide chloride a) 5-Amino-2,4,6-triiodoisophthalic acid (2-acetoxy-ethyl) monoamide 128.8 g (200 mmol) of 5-amino-2,4,6-triiodoisophthalic acid (2-hydroxy-ethyl) monoamide (DOS 16 43 440) is suspended in 1.2 liters of dioxane, 61.25 g (600 mmol) acetic anhydride and 2.44 g (20 mmol) of 4-dimethylaminopyridine are added and the suspension is stirred at 80° C. After about 2 hours an approximately clear solution is present and the reaction is complete It is stirred for 12 hours at room temperature. The product crystallizes out. It is suctioned off, washed with dioxane and dried in a vacuum at 50° C. The yield is 122.7 g (190.5 mmol)=95.3% of theory.

b) 5-Amino-2,4,6-triiodoisophthalic acid (2-acetoxy-ethyl) monoamide chloride 117.2 g (181.94 mmol) of 5-amino-2,4,6-triiodoisophthalic acid (2-acetoxy-ethyl) monoamide is suspended in 586 ml of dichloroethane, 64.94 g (545.82 mmol) of thionyl chloride is added and the suspension is heated to boiling. After 45 minutes a clear solution is present, after 55 minutes the sulfinylimide of the product begins to precipitate from it in a crystalline form. After 2 hours the reaction is complete. It is cooled to room temperature, the crystallizate is suctioned off, suspended in 400 ml of dichloroethane, to this suspension 49.4 g (172.7 mmol) of soda decahydrate is added and the suspension is stirred for 5 hours at room temperature. The solid is then suctioned off and boiled for 2 hours with 1 liter of tetrahydrofuran. In this case the product goes into solution and the inorganic salts remain undissolved. The tetrahydrofuran solution is concentrated to about 500 ml by evaporation, and the product is precipitated in a crystalline form. The yield is 106.73 g (161 mmol)=88.6% of theory.

The subsequent dimerization to the compounds of general formula II takes place according to processes known in the literature (e.g., EP 0 033 426).

EXAMPLE 1

Malonic acid bis-[3-(2,3-dihydroxy-N-methyl-propylcarbamoyl)-5-(2,3-dihydroxy-propylcarbamoyl)-2,4,6-triiodo N-methylanilide]

a) Malonic acid bis-[3-(chlorocarbonyl-2,4,6-triiodo-5-(2,3-diacetoxy-propylcarbamoyl) anilide]

79.3 g (108 mmol) of 5-amino-2,4,6-triiodoisophthalic acid (2,3-diacetoxypropyl) amide chloride is dissolved in 250 ml of toluene, the solution is heated to 90° C. and 8.81 g (50 mmol) of malonyl chloride is added. A bright crystalline precipitate quickly results. After 15 minutes the heating is removed and the batch is allowed to come to room temperature. The crystalline reaction product is suctioned off, washed with toluene and dried in a vacuum at 50° C. The yield is 69.8 g (45.4 mmol) =84.1% of theory.

b) Malonic acid bis-[3-(2,3-dihydroxy-N-methyl-propylcarbamoyl)-5-(2,3-dihydroxy-propylcarbamoyl)-2,4,6-triiodoanilide]

65 g (42.3 mmol) of malonic acid bis-[3-chlorocarbonyl-2,4,6-triiodo-5-(2,3-diacetoxy-propylcarbamoyl) anilide] is dissolved in 650 ml of acetone, mixed with 36.3 g (126.9 mmol) of soda decahydrate and 13.3 g (126.9 mmol) of N-methyl-aminopropanediol-2,3 and the suspension is refluxed for 2 hours. The reaction mixture is then cooled to room temperature, the solid precipitate is suctioned off, the filtrate is concentrated by evaporation, the residue is dissolved in 300 ml of water, saponified under pH control with concentrated sodium hydroxide solution, neutralized with hydrochloric acid and desalted with ion-exchangers. The aqueous eluate from the ion-exchanger is evaporated to dryness. The yield is 58.62 g (38.9 mmol)=92% of theory of amorphous solid.

c) Malonic acid bis-[3-(2,3-dihydroxy-N-methyl-propylcarbamoyl)-5-(2,3-dihydroxy-propylcarbamoyl)-2,4,6-triiodo-N-methyl anilide]

1.48 g (64.3 mmol) of sodium is dissolved in 62 ml of methanol, the solution is mixed with 62 ml of propanediol-1,2, in this solution 23.1 g (15.3 mmol) of malonic acid bis-[3-(2,3-dihydroxy-N-methyl-propylcarbamoyl)-5-(2,3-dihydroxy-propylcarbamoyl)-2,4,6-triiodoanilide] is dissolved and stirred for 4 hours at 50° C.

The methanol is then distilled off at normal pressure, 7.72 g (61.2 mmol) of dimethyl sulfate is added and stirred for 20 hours at 50° C. The reaction solution is then cooled to room temperature, precipitated in 1 liter of acetone, the precipitate is suctioned off, dissolved in water and desalted on ion-exchangers. The eluate is evaporated to amorphous solid. The yield is 21.12 g (13.8 mmol)=90% of theory.

EXAMPLE 2

Malonic acid bis-{3-(2,3-dihydroxy-propylcarbamoyl)-5-[bis(2-hydroxyethyl)-carbamoyl]-2,4,6-triiodo-N-methyl anilide} a) Malonic acid bis-[3-(2,3-dihydroxy-propylcarbamoyl)-5-[bis(2-hydroxyethyl)-carbamoyl]-2,4,6-triiodoanilide]

153.7 g (100 mmol) of malonic acid bis-[3-chlorocarbonyl-2,4,6-triiodo-5-(2,3-diacetoxy-propylcarbamoyl) anilide] is dissolved at room temperature in 1537 ml of acetone, the solution is mixed with 85.84 g (300 mmol) of soda decahydrate and a solution of 31.54 g (300 ml) of diethanolamine in 100 ml of acetone is instilled into this suspension in the course of about 15 minutes. The suspension is then refluxed for 1.5 hours. After expiration of this period the reaction is complete. The solid bottom sediment is suctioned off, the filtrate is evaporated to an oil, this oil is dissolved in 300 ml of water and is kept at 50° C. with 32% sodium hydroxide solution at pH 12 until the pH remains at 12 and thin-film chromatography indicates complete saponification of the acetate groups. The aqueous solution is neutralized with aqueous hydrochloric acid and desalted on ion-exchangers. The aqueous eluate is evaporated to dryness. The yield is 130 g (86.3 mmol)=86.3% of theory as colorless amorphous solid.

b) Malonic acid bis-{3-(2,3-dihydroxy-propylcarbamoyl)-5-[bis(2-hydroxyethyl)-carbamoyl]-2,4,6-triiodo-N-methyl anilide}

4.6 g (200 mmol) of sodium is dissolved in a mixture of 200 ml of methanol and 200 ml of propanediol-1,2, to this solution is added 75.3 g (50 mmol) of malonic acid bis-(3-(2,3-dihydroxy-propylcarbamoyl)-5-[bis(2-hydroxyethyl)-carbamoyl]-2,4,6-triiodoanilide}, is stirred for 3 hours at 50° C. and the methanol is then distilled off at normal pressure. Afterward the reaction solution is mixed with 28.67 g (200 mmol) of methyl iodide and stirred for 24 hours at 50° C. Thin-film chromatography then shows complete reaction. The reaction solution is cooled to room temperature, is stirred into 2 liters of acetone, the amorphous precipitate is suctioned off, dissolved in water and the solution is desalted on ion-exchangers. The aqueous eluate evaporated to dryness yields 60.2 g (39.25 mmol)=78.5% of theory of a colorless amorphous solid.

EXAMPLE 3

Malonic acid bis-{3-(2,3-dihydroxy-propylcarbamoyl)-5-[(1RS,2SR)-2,3-dihydroxy-1-hydroxymethylpropyl-carbamoyl]-2,4,6-triiodo-N-methyl anilide} a) Malonic acid bis-{3-(2,3-dihydroxy-propylcarbamoyl)-5-[(1RS,2SR)-2,3-dihydroxy-1-hydroxymethylpropyl-carbamoyl]-2,4,6-triiodoanilide}

153.7 g (100 mmol) of malonic acid bis-[3-chlorocarbonyl-2,4,6-triiodo-5-(2,3-diacetoxy-propylcarbamoyl) anilide] is dissolved in 1.52 liters of acetone at room temperature, 85.84 g (300 mmol) of soda decahydrate and 48.36 g (300 mmol) of 6-amino-2,2-dimethyl-1,3-dioxepin-5-ol are added and refluxed for 2 hours. The reaction mixture is then cooled to room temperature, the solid precipitate is suctioned off, the filtrate is concentrated by evaporation, the residue is dissolved in 300 ml of water and with pH control at 50° C. the acetate groups are hydrolyzed at pH 12 and the ketals at pH 1. Then the solution is made neutral and desalted on ion-exchangers. The aqueous eluate is evaporated to dryness and yields 134.28 g (87.3 mmol)=87.3% of theory of amorphous solid.

b) Malonic acid bis-{3-(2,3-dihydroxy-propylcarbamoyl)-5-[(1RS,2SR)-2,3-dihydroxy-1-hydroxy-methylpropyl-carbamoyl]-2,4,6-triiodo-N-methyl anilide}

9.2 g (400 mmol) of sodium is dissolved in a mixture of 400 ml of methanol and 400 ml of propanediol-1,2; to this solution is added 153.8 g (100 mmol) of malonic acid bis-{3-(2,3-dihydroxy-propylcarbamoyl)-5-[(1RS,2SR)-2,3-dihydroxy-1-hydroxy-methylpropyl-carbamoyl]-2,4,6-triiodoanilide}, is stirred for 3 hours at 50° C. and then the methanol is distilled off at normal pressure. Afterward the reaction solution is mixed with 57.35 g (400 mmol) of methyl iodide and stirred for 24 hours at 50° C. TLC then shows complete reaction. The reaction solution is cooled to room temperature, stirred into 4 liters of acetone, the amorphous precipitate of the product is suctioned off, dissolved in water and the aqueous solution is desalted on ion-exchangers. The eluate evaporated to dryness yields 116.84 g (74.6 mmol)=74.6% of theory of a colorless amorphous solid.

EXAMPLE 4

Malonic acid bis-[3-(2-hydroxy-N-methyl-ethylcarbamoyl)-5-(2,3-dihydroxy-propylcarbamoyl)-2,4,6-triiodo-N-(2-hydroxy-ethyl) anilide]

a) Malonic acid bis-[3-(2-hydroxy-N-methyl-ethylcarbamoyl)-5-(2,3-dihydroxy-propyl-carbamoyl) 2,4,6-triiodoanilide]

153.7 g (100 mmol) of malonic acid bis-[3-chlorocarbonyl-5-(2,3-diacetoxy-propyl-carbamoyl)-2,4,6-triiodoanilide] is dissolved in 1.52 liters of acetone at room temperature, 85.84 g (300 mmol) of soda decahydrate and 22.53 g (300 mmol) of N-methyl-ethanolamine are added and refluxed for 2 hours. The suspension is then cooled to room temperature, the solid precipitate is suctioned off, the filtrate concentrated by evaporation, the residue is dissolved in 300 ml of water and with pH control at 50° C. the acetate groups are saponified at pH 12. Then the solution is neutralized and desalted on ion-exchangers. The aqueous eluate is evaporated to dryness and yields 109.1 g (75.5 mmol)=75.7% of theory of a colorless amorphous solid.

b) Malonic acid bis-[3-(2-hydroxy-N-methyl-ethylcarbamoyl)-5-(2,3-dihydroxy-propylcarbamoyl)-2,4,6-triiodo-N-(2-hydroxy-ethyl) anilide]

4.29 g (186.76 mmol) of sodium is dissolved in a mixture of 193 ml of methanol and 193 ml of propanediol-1,2, 64.3 g (44.46 mmol) of malonic acid bis-[3-(2-hydroxy-N-methyl-ethyl-carbamoyl)-5-(2,3-dihydroxy-propylcarbamoyl)-2,4,6-triiodoanilide]is added, the solution is stirred for 3 hours at 50° C. and the methanol is then distilled off at normal pressure. Afterward the reaction solution is mixed with 14.61 g (177.84 mmol) of chloroethanol and stirred for 24 hours at 50° C. Thin-film chromatography then shows complete reaction. The reaction solution is cooled to room temperature, stirred into 3 liters of acetone, the amorphous precipitate of the product is suctioned off, dissolved in water and the aqueous solution is desalted on ion-exchangers. The eluate evaporated to dryness yields 51.57 g (33.68 (mmol)=75.7% of theory of a colorless amorphous solid.

EXAMPLE 5

Malonic acid bis-[3-(2,3-dihydroxy-N-methyl-propylcarbamoyl)-5-(2-hydroxy-ethyl-carbamoyl)-2,4,6-triiodo-N-methylanilide]

a) Malonic acid bis-[3-chlorocarbonyl-2,4,6-triiodo-(2-acetoxy-ethylcarbamoyl) anilide 155.9 g (235.4 mmol) of 5-amino-2,4,6-triiodoisophthalic acid (2-acetoxy-ethyl)-monoamide chloride is suspended at room temperature in 780 ml of dioxane, heated to 80° C., until a solution has resulted. To this is added 20.32 g (141.2 mmol) of malonylchloride and stirred for 12 hours at 80° C. The product increasingly crystallizes out from the reaction solution in this period. It is cooled to room temperature, the crystallizate is suctioned off, washed with dioxane and dried in a vacuum at 50° C. for 24 hours. The yield is 123.26 g (88.5 mmol)=75.2% of theory.

b) Malonic acid bis-[3-(2,3-dihydroxy-N-methyl-propylcarbamoyl)-5-(2-hydroxy-ethylcarbamoyl)-2,4,6-triiodoanilide]

69.64 g (50 mmol) of malonic acid bis-[3-chlorocarbonyl-2,4,6-triiodo-(2-acetoxy-ethylcarbamoyl) anilide] is dissolved in 105 ml of dimethylformamide and the mixture of 15.78 g (150 mmol) of N-methyl-aminopropanediol-1,2 and 15.18 g (150 mmol) of triethylamine, dissolved in 10 ml of DMF, is instilled into this solution at room temperature. After four hours of stirring at room temperature the reaction is complete. The hydrochloride of the triethylamine is filtered off, the filtrate is stirred into 2 liters of methylene chloride, the precipitate of the product is suctioned off, dissolved in 200 ml of water, this solution is saponified at 50° C. and pH 12, neutralized with hydrochloric acid and desalted on ion-exchangers. The eluate evaporated to dryness yields 56.1 g (38.8 mmol)=77.6% of theory of a colorless amorphous solid.

c) Malonic acid bis-[3-(2,3-dihydroxy-N-methyl-propylcarbamoyl)-5-(2-hydroxy-ethylcarbamoyl)-2,4,6-triiodo-N-methyl anilide]

4.6 g (200 mmol) of sodium is dissolved is a mixture of 200 ml of methanol and 200 ml of propanediol-1,2; to the solution is added 72.3 g (50 mmol) of malonic acid bis-[3-(2,3-dihydroxy-N-methyl-propylcarbamoyl)-5-(2-hydroxy-ethylcarbamoyl)-2,4,6-triiodoanilide], the solution is stirred for 3 hours at 50° C., the methanol is then distilled off at normal pressure, 28.4 g (200 mmol) of methyl iodide is added and stirred for 24 hours at 50° C. According to thin-film chromatography the reaction is complete after the expiration of this period. The reaction solution is cooled to room temperature, stirred into 3 liters of acetone, the precipitate of the product is suctioned off, dissolved in water and the aqueous solution is desalted on ion-exchangers. The eluate evaporated to dryness contains 60.06 g (39.15 mmol) = 78.3% of theory of a colorless amorphous solid.

EXAMPLE 6

Malonic acid bis-{3-(2,3-dihydroxy-carbamoyl)-5-(2-hydroxyethyl-carbamoyl)-2,4,6-triiodo-N-(2,3-dihydroxy-propyl) anilide} a) Malonic acid bis{3(2,3-dihydroxy-propylcarbamoyl)-5-(2-hydroxyethyl-carbamoyl)-2,4,6-triiodoanilide}

100 g (68.45 mmol) of malonic acid bis-[3-chlorocarbonyl-2,4,6-triiodo-5-(2,3-diacetoxy-propylcarbamoyl) anilide] is dissolved in 1000 ml of acetone, the solution is mixed with 59.54 g (208.1 mmol) of soda decahydrate and 11.29 g (184.82 mmol) of ethanolamine, dissolved in 50 ml of acetone, is instilled into this suspension in the course of about 15 minutes. After the addition of the amine is completed the suspension is refluxed for 2 hours. According to thin-film chromatography the reaction was then complete, the product is in the precipitate of the inorganic salts. The precipitate is suctioned off, suspended in water, the slightly water-soluble intermediate product is suctioned off, the filter residue is suspended in water, saponified with sodium hydroxide solution, neutralized, the aqueous solution is desalted on ion-exchangers and the eluate is evaporated to dryness. Yield 84.73 g (59.76 mmol) = 87.3% of theory as colorless amorphous solid.

b) Malonic acid bis-{3-(2,3-dihydroxy-propylcarbamoyl)-5-(2-hydroxyethyl-carbamoyl)-2,4,6-triiodo-N-(2,3-dihydroxy-propyl) anilide}

9.2 g (400 mmol) of sodium is dissolved in a mixture of 400 ml of methanol and 400 ml of propanediol-1,2, to this solution is added 141.8 g (100 mmol) of malonic acid bis-[3-(2,3-dihydroxy-propylcarbamoyl)-5-(2-hydroxyethyl-carbamoyl)-2,4,6-triiodoanilide], stirred for 3 hours at 50° C. and the methanol is then distilled off at normal pressure. The reaction solution is mixed with 32.86 g (300 mmol) of chloropropanediol-2,3 and stirred for 24 hours at 50° C. According to thin-film chromatography the reaction is complete. For working up, the reaction solution is stirred into 4 liters of acetone, the precipitate of the product is suctioned off, dissolved in water, desalted on ion-exchangers, the aqueous eluate is evaporated to dryness The yield is 127.2 g (81.2 mmol) = 81.2% of theory of the product as colorless amorphous solid.

EXAMPLE 7

Hydroxymalonic acid bis-[3-(2,3-dihydroxy-propylcarbamoyl)-5-(2-hydroxyethyl-carbamoyl)-2,4,6-triiodo-N-(2,3-dihydroxy-propyl) anilide]

a) Acetoxymalonic acid bis-[3-chlorocarbonyl-2,4,6-triiodo-5-(2,3-diacetoxy-propylcarbamoyl) anilide]

73.4 g (100 mmol) of 5-amino-2,4,6-triiodoisophthalic acid (2,3-diacetoxy-propyl) amide chloride is dissolved in 250 ml of toluene, the solution is warmed to 90° C. and 10.12 g (55 mmol) of acetoxymalonic acid dichloride (produced analogously to O-acetyl-lactyl chloride, Filachione et al., JACS 72, 410 [1950]) in instilled. A crystalline precipitate of the product quickly results. After 15 minutes the heating bath is removed, it is cooled to room temperature, the crystallizate is suctioned off, washed with toluene and dried in a vacuum at 50° C. The yield is 55.97 g (36.9 mmol) = 73.8% of theory.

b) Hydroxymalonic acid bis-[3-(2,3-dihydroxy-propylcarbamoyl)-5-(2-hydroxyethyl-carbamoyl)-2,4,6-triiodoanilide]

84.95 g (56 mmol) of acetoxymalonic acid bis-[3-(2,3-diacetoxy-propylcarbamoyl)-5-chlorocarbonyl-2,4,6-triiodoanilide] is dissolved in 170 ml of dioxane, 41.66 g (145.6 mmol) of soda decahydrate and 8.9 g (145.6 mmol) of ethanolamine are added and refluxed for 2 hours. The reaction solution is then cooled to room temperature, the precipitate is suctioned off, the filtrate is concentrated by evaporation, the residue is dissolved in 250 ml of water, saponified with pH control at 50° C. with concentrated sodium hydroxide solution, neutralized with hydrochloric acid and desalted on ion-exchangers. The aqueous eluate is evaporated to dryness. The yield is 71 g (49.5 mmol) = 88.4% of theory.

c) Hydroxymalonic acid bis-[3-(2,3-dihydroxy-propylcarbamoyl)-5-(2-hydroxyethyl-carbamoyl)-2,4,6-triiodo-N-(2,3-dihydroxy-propyl) anilide]

4.6 g (200 mmol) of sodium is dissolved in a mixture of 200 ml of methanol and 200 ml of propanediol-1,2, to this solution is added 71.7 g (50 mmol) of hydroxymalonic acid bis-[3-(2,3-dihydroxy-propylcarbamoyl)-5-(2-hydroxyethyl-carbamoyl)-2,4,6-triiodoanilide], it is stirred for 3 hours at 50° C. and the methanol is then distilled off at normal pressure. The reaction solution is then mixed with 16.43 g (150 mmol) of chloropropanediol-2,3 and stirred for 24 hours at 50° C. For working up, it is stirred into 3 liters of methylene chloride, the precipitate is suctioned off, dissolved in 200 ml of water, desalted on ion-exchangers, the eluate is evaporated to dryness and the residue is dried in a vacuum at 50° C. The yield is 60.91 g (38.5 mmol) = 77% of theory.

EXAMPLE 8

Hydroxymalonic acid
bis-[3-(2-hydroxy-1-hydroxymethylethyl-carbamoyl)-5-(2,3-dihydroxy-propylcarbamoyl)-2,4,6-triiodo-N-methyl anilide]

a) Hydroxymalonic acid
bis-[3-(2-hydroxy-1-hydroxymethylethyl-carbamoyl)-5-(2,3-dihydroxy-propylcarbamoyl)-2,4,6-triiodoanilide]

75.85 g (50 mmol) of acetoxymalonic acid bis-[3-(2,3-diacetoxy-propyl-carbamoyl)-5-chlorocarbonyl-2,4,6-triiodoanilide] is dissolved in 150 ml of dioxane, 37.2 g (130 mmol) of soda decahydrate and 11.84 g (130 mmol) of serinol are added and refluxed for 2 hours. The reaction solution is then cooled to room temperature, the solid is suctioned off, the filtrate is concentrated by evaporation, the residue is dissolved in 250 ml of water, saponified with pH control at 50° C. with concentrated sodium hydroxide solution, neutralized with hydrochloric acid and desalted on ion-exchangers. The eluate, evaporated to dryness, contains 64.62 g (43.25 mmol)=86.5% of theory of colorless solid.

b) Acetoxymalonic acid
bis-[3-(2-acetoxy-1-acetoxymethylethyl-carbamoyl)-5-(2,3-diacetoxypropyl -carbamoyl)-2,4,6-triiodoanilide]

112.06 g (75 mmol) of hydroxymalonic acid bis-[3-(2-hydroxy-1-hydroxymethylethyl-carbamoyl)-5-(2,3-dihydroxy-propyl-carbamoyl)-2,4,6-triiodoanilide] is suspended in 300 ml of ethyl acetate, 137.8 g (1.35 mol) of acetic anhydride and 1.65 g (13.5 mmol) of 4-dimethylaminopyridine are added and refluxed for 5 hours. Then a clear solution is present and the reaction is quantitative. The solution is mixed with 31.1 g (0.675 mol) of ethanol and refluxed for another hour. Then the solvent is largely distilled off, the residue is stirred with 300 ml of water, the product thus solidly precipitating is suctioned off and dried. Yield 115.6 g (61.7 mmol)=82.3% of theory.

c) Hydroxymalonic acid
bis-[3-(2-hydroxy-1-hydroxmethylethyl-carbamoyl)-5-(2,3-dihydroxy-propylcarbamoyl)-2,4,6-triiodo-N-methyl anilide]

4.6 g (200 mmol) of sodium is dissolved in a mixture of 200 ml of methanol and 200 ml of ethylene glycol dimethyl ether, 93.62 g (50 mmol) of acetoxymalonic acid bis-[3-(2-acetoxy-1-acetoxymethylethyl-carbamoyl)-5-(2,3-diacetoxy-propyl-carbamoyl)-2,4,6-triiodoanilide is added, stirred for 3 hours at 50° C., the methanol is then distilled off at normal pressure, 21.3 g (150 mmol) of methyl iodide is added to the remaining solution and stirred for 24 hours at 50° C. The reaction solution is then filtered, the filtrate is concentrated by evaporation, the residue is suspended in water, saponified with sodium hydroxide solution, neutralized, the solution is desalted on ion-exchangers and the eluate is evaporated to dryness. 55.25 g (36.3 mmol)=72.6% of theory of colorless solid is obtained.

EXAMPLE 9

Hydroxymalonic acid
bis-[3-(2-hydroxy-N-methyl-ethylcarbamoyl)-5-(2,3-dihydroxy-propyl-carbamoyl)-2,4,6-triiodo-N-(2-hydroxy-ethyl anilide]

a) Malonic acid
bis-[3-(2-acetoxy-N-methyl-ethylcarbamoyl)-5-(2,3-diacetoxy-propylcarbamoyl)-2,4,6-triiodo-N-(2-acetoxy-ethyl) anilide]

76.78 g (50 mmol) of malonic acid bis-[3-(2-hydroxy-N-methyl-ethylcarbamoyl)-5-(2,3-dihydroxy-propyl-carbamoyl)-2,4,6-triiodo-N-(2-hydroxy-ethyl anilide] (see example 4) is suspended in 400 ml of dioxane, 122.5 g (1.2 mol) of acetic anhydride and 0.61 g (5 mmol) of 4-dimethylaminopyridine are added and the mixture is warmed to 80° C. After about 1 hour, a clear solution is present, after 2 hours the acetylation is complete. The excess acetic anhydride is converted by addition of 36.85g (800 mmol) of ethanol into ethyl acetate, the solution is concentrated under reduced pressure and the concentrate is stirred into 2 liters of water. The resulting flocculent precipitate is suctioned off, washed with water and dried in a vacuum at 50° C. The yield is 80.8 g (43.2 mmol)=86.4% of theory.

b) Hydroxymalonic acid
bis-[3-(2-hydroxy-N-methyl-ethylcarbamoyl)-5-(2,3-dihydroxy-propylcarbamoyl)-2,4,6-triiodo-N-(2-hydroxy-ethyl) anilide]

74.8 g (40 mmol) of malonic acid bis-[3-(2-acetoxy-N-methyl-ethylcarbamoyl)-5-(2,3-diacetoxy-propylcarbamoyl)-2,4,6-triiodo-N-(2-acetoxy-ethyl) anilide] is dissolved in 250 ml of acetic acid, the solution is warmed to 100° C. and 17.73 g (40 mmol) of lead tetraacetate is added in several portions within about 45 minutes. When the addition is completed, it is kept for 2 more hours at 100° C. A part of the acetic acid is then distilled off at reduced pressure, the concentrated solution is cooled to room temperature and stirred into 3 liters of water. The resulting product precipitates as flocculent precipitate. This is suctioned off, washed with water and, moist with water, is dissolved in 300 ml of ethanol. 32% sodium hydroxide solution is added to this solution at 50° C. until thin-film chromatography indicates complete hydrolysis of the acetyl groups. The solution is then neutralized, the ethanol is largely distilled off at reduced pressure, replaced with 200 ml of water and this solution is desalted on ion-exchangers. By concentration by evaporation of the aqueous eluate 38.13 g (24.6 mmol)=61.5% of theory of the product is obtained.

EXAMPLE 10

Methoxymalonic acid
bis-[3-(2-hydroxy-1-hydroxymethyl-ethyl-carbamoyl)-5-(2,3 dihydroxy-propylcarbamoyl)-2,4,6-triiodo-N-methyl anilide]

a) Methoxymalonic acid
bis-[3-chlorocarbonyl-2,4,6-triiodo-5-(2,3-diacetoxy-propyl-carbamoyl) anilide]

73.4 g (100 mmol) of 5-amino-2,4,6-triiodoisophthalic acid (2,3-diacetoxy-propyl) amide chloride is dissolved in 250 ml of toluene, the solution is warmed to 90° C. and 8.52 g (55 mmol) of methoxymalonyl chloride is instilled. A crystalline precipitate of the product quickly is formed. After 15 minutes, the heating bath is removed, it is cooled to room temperature, the crystallizate is suctioned off, washed with toluene and dried in a vacuum at 50° C. The yield is 57.07 g (38.15 mmol) = 76.3% of theory.

b) Methoxymalonic acid bis-[3-(2-hydroxy-1-hydroxymethylethyl-carbamoyl)-5-(2,3-dihydroxy-propylcarbamoyl)-2,4,6-triiodoanilide]

74.8 g (50 mmol) of methoxymalonic acid bis-[3-chlorocarbonyl-5-(2,3-diacetoxy propylcarbamoyl)-2,4,6-triiodoanilide] is dissolved in 150 ml of dioxane, 37.2 g (130 mmol) of soda decahydrate and 11.84 g (130 mmol) of serinol are added and stirred for 2 hours at 50° C. The reaction mixture is then cooled to room temperature, the solid is suctioned off, the filtrate is concentrated by evaporation, the residue is dissolved in 250 ml of water, saponified with pH control at 50° C. with concentrated sodium hydroxide solution, neutralized with hydrochloric acid and desalted on ion-exchangers. The aqueous eluate evaporated to dryness contains 66.58 g (44.15 mmol) = 88.3% of theory of colorless amorphous solid.

c) Methoxymalonic acid bis-[3-(2-hydroxy-1-hydroxymethylethyl-carbamoyl)-5-(2,3-dihydroxy-propylcarbamoyl)-2,4,6-triiodo-N-methyl anilide]

4.6 g (200 mmol) of sodium is dissolved in a mixture of 200 ml of methanol and 200 ml of propanediol-1,2, 75.4 g (50 mmol) of methoxymalonic acid bis-[3-(2-hydroxy-1-hydroxymethylethyl-carbamoyl)-5-(2,3-dihydroxy-propylcarbamoyl)-2,4,6-triiodoanilide] is added, stirred for 3 hours at 50° C., the methanol is then distilled off at normal pressure, 21.3 g (150 mmol) of methyl iodide is added to the remaining solution and stirred for 24 hours at 50° C. The reaction solution is then cooled to room temperature and stirred into 2 liters of methylene chloride. In this case the product precipitates at pasty mass. It is decanted from this, dissolved in 200 ml of water and desalted on ion-exchangers. 56.4 g (36.7 mmol) = 73.4% of theory of the title compound is obtained as amorphous solid.

EXAMPLE 11

2,3-Dihydroxy succinic acid bis-[3-(2,3-dihydroxy-propylcarbamoyl)-5-(2-hydroxy-ethylcarbamoyl)-2,4,6-triiodo-N-(2-hydroxyethyl) anilide]

a) 2,3-Diacetoxy succinic acid bis-[3-chlorocarbonyl-2,4,6-triiodo-5-(2,3-diacetoxy-propylcarbamoyl) anilide]

73.4 g (100 mmol) of 5-amino-2,4,6-triiodoisophthalic acid (2,3-diacetoxy-propyl) amide chloride is dissolved in 250 ml of toluene, the solution is warmed to 90° C. and 14.91 g (55 mmol) of 2,3-diacetyl succinic acid dichloride (produced according to D. Seebach et al. Ber. 1980, 1691) is added. A crystalline precipitate of the product quickly results. After 30 minutes, it is cooled to room temperature and the crystallizate suctioned off, washed with toluene and dried in a vacuum at 50° C. The yield is 59.43 g (35.65 mmol) = 71.3% of theory.

b) 2,3-Dihydroxy succinic acid bis-[3-(2,3-dihydroxy-propylcarbamoyl)-5-(2-hydroxy-ethylcarbamoyl)-2,4,6-triiodoanilide]

75.02 g (45 mmol) of 2,3-diacetoxy succinic acid bis-[3-(2,3-diacetoxypropyl-carbamoyl)-5-chlorocarbonyl-2,4,6-triiodoanilide] is dissolved in 250 ml of dioxane, 15.7 g (67.5 mmol) of soda decahydrate and 4.12 g (67.5 mmol) of ethanolamine are added and stirred for 2 hours at 50° C. The suspension is then cooled to room temperature, the precipitate is suctioned off, the filtrate is concentrated by evaporation, the residue is suspended in 250 ml of water, saponified at 50° C. with pH control with concentrated sodium hydroxide solution, neutralized with hydrochloric acid and desalted on ion-exchangers. The aqueous eluate is evaporated to dryness and yields 57.65 g (39.4 mmol) 87.6% of theory of the compound.

c) 2,3-Dihydroxy succinic acid bis [2,3-dihydroxy-propylcarbamoyl)-5-(2-hydroxy-ethyl-carbamoyl)-2,4,6-triiodo-N-(2-hydroxy-ethyl) anilide]

4.6 g (200 mmol) of sodium is dissolved in a mixture of 200 ml of methanol and 200 ml of propanediol-2,3 to this solution is added 73.2 g (50 mmol) of 2,3-dihydroxy succinic acid bis-[3-(2,3-dihydroxy-propylcarbamoyl)-5-(2-hydroxy-ethylcarbamoyl)-2,4,6-triiodoanilide, stirred for 3 hours at 50° C. and the methanol is then distilled off at normal pressure. The reaction solution is then mixed with 12.1 g (150 mmol) of chloroethanol and stirred for 24 hours at 50° C. To isolate the product the reaction solution, after cooling to room temperature, is precipitated in 3 liters of methylene chloride, the precipitate is suctioned off, dissolved in water and desalted on ion-exchangers. The eluate evaporated to dryness yields 81.2 g (52.3 mmol) = 72.3% of theory of the desired compound.

EXAMPLE 12

Hydroxymalonic acid bis-[3-(2,3-dihydroxy-N-methyl-propylcarbamoyl)-5-(2,3-dihydroxy-propylcarbamoyl)-2,4,6-triiodo-N-methyl anilide]

a) 5-Methylamino-2,4,6-triiodoisophthalic acid (2,3-diacetoxy-propyl) monoamide chloride 122 g (200 mmol) of 5-methylamino-2,4,6-triiodoisophthalic acid dichloride is dissolved in 400 ml of dioxane, 71.5 g (250 mmol) $Na_2CO_3$ decahydrate and 18.2 g (200 mmol) of 2,3-dihydroxy propylamine are added and the mixture is stirred for 3 hours at room temperature. The precipitate is then suctioned off, the filtrate is evaporated to a foam, this is taken up in 200 ml of dioxane, 36.75 g (360 mmol) of acetic anhydride and 2.44 g (20 mmol) of 4-dimethylaminopyridine are added and stirred for 3 hours at 80°. A homogeneous solution results. The reaction solution is evaporated in a vacuum to a foam, this is dissolved in 200 ml of acetone and chromatographed on 2 kg of silica gel 60 (Merck) with hexane/ethyl acetate (ethyl acetate portion 20-50% linearly increased). The corresponding fractions are collected and, after concentration by evaporation, yield 65.12 g (87 mmol) = 43.5% of theory of the compound as amorphous solid.

b) Benzyloxy malonic acid bis-[3-chlorocarbonyl-2,4,6-triiodo-5(2,3-diacetoxy-propylcarbamoyl)-N-methyl anilide]

60 g (80 mmol) of 5-methylamino-2,4,6-triiodoisophthalic acid (2,3-diacetoxypropyl) monoamide chloride is suspended in 600 ml of toluene and the suspension is heated to 100° C. It consists of a clear solution. To this is added 9.88 (40 mmol) of benzyloxy malonic acid dichloride (produced analogously to Hammond et al. Soc. 1957, 1062). After a few minutes the bisanilide precipitates out as crystalline precipitate. After 30 minutes the heating is removed, and it is cooled to room temperature, the precipitate is suctioned off and dried in a vacuum at 50° C. for 24 hours. 48.46 g (29.3 mmol)=73.2% of theory of bisanilide is obtained as crystallizate. Mp greater than 350° C.

c) Benzyloxy malonic acid bis-[3-(2,3-diacetoxy-N-methyl-propylcarbamoyl)-5-(2,3-diacetoxy-propylcarbamoyl)-2,4,6-triiodo-N-methyl anilide]

82.76 g (50 mmol) of benzyloxy malonic acid bis-[3-chlorocarbonyl-2,4,6-triiodo-5-(2,3-diacetoxy-propyl-carbamoyl)-N-methyl anilide] is dissolved in 830 ml of acetone, 18.6 g (65 mmol) of $Na_2CO_3 \times 10\ H_2O$, 6.3 g (60 mmol) of N-methylamino-propanediol-2,3 are added and refluxed for 2 hours. The reaction is then complete. It is cooled to room temperature, the solid precipitate is suctioned off, filtrate is evaporated in a vacuum to an oil, this is dissolved in 300 ml of dioxane, the remaining water is removed by azeotropic distillation, the dioxane thus consumed is replaced, 36.75 g (360 mmol) of acetic anhydride and 0.61 g (5 mmol) of 4-dimethylaminopyridine is added and stirred for 3 hours at 80° C. The solvent is distilled off in a vacuum, the oily residue is dissolved in ethyl acetate and chromatographed on 850 g of silica gel 60 with hexane/ethyl acetate 1:1. The corresponding fractions are collected and evaporated in a vacuum to a solid foam. The yield is 77.1 g (39 mmol)=78% of theory.

d) Hydroxymalonic acid bis-[3-(2,3-dihydroxy-N-methyl-propylcarbamoyl)-5-(2,3-dihydroxy-propylcarbamoyl)-2,4,6-triiodo-N-methyl anilide]

39.5 g (20 mmol) of benzyloxy malonic acid bis-[3-(2,3-diacetoxy-N-methyl-propylcarbamoyl)-5-(2,3-diacetoxy-propylcarbamoyl)-2,4,6-triiodo-N-methyl anilide] is dissolved in 200 ml of abs. ethanol and mixed with a total of 1.38 g (60 mmol) of sodium in small portions. The solution is stirred at room temperature for 12 hours. The reaction solution is then evaporated in a vacuum to about half, mixed with 100 ml of water and saponified with concentrated NaOH at 50° C. at pH 10–12. On completion of the saponification, it is neutralized with concentrated hydrochloric acid, evaporated in a vacuum to an oil, this is dissolved in 100 ml of water and the solution is desalted on ion-exchangers. The eluate is evaporated to a foam in a vacuum and this is dried 24 hours in a vacuum at 50° C. The yield is 23.25 g (15 mmol)=75% of theory.

EXAMPLE 13

Hydroxymalonic acid bis-[3-(2,3-dihydroxy-N-methyl-propylcarbamoyl)-5-(2,3-dihydroxy-propylcarbamoyl)-2,4,6-triiodo-N-methyl anilide]

a) Bromomalonic acid bis-[3-chlorocarbonyl-2,4,6-triiodo-5-(2,3-diacetoxy-propylcarbamoyl)-N-methyl anilide]

37.42 g (50 mmol) of 5-methylamino-2,4,6-triiodoisophthalic acid (2,3-diacetoxypropyl) monoamide chloride is suspended in 370 ml of toluene and the suspension is heated to 100° C. A clear solution results. To this is added 5.5 g (25 mmol) of bromomalonic acid chloride (Ber. 1908, 4465). After some minutes the bisanilide crystallizes out as crystalline precipitate. After 30 minutes the heating is removed, it is cooled to room temperature, the precipitate is suctioned off and dried at 50° C. in a vacuum for 24 hours. 31.32 g (19.05 mmol)=76.2% of theory of the bisanilide is obtained as crystallizate. Mp greater than 350° C.

b) Bromomalonic acid bis-[3-(2,3-diacetoxy-N-methyl-propylcarbamoyl)-5-(2,3-diacetoxy-propylcarbamoyl)-2,4,6-triiodo-N-methyl anilide 24.66 g (15 mmol) of bromomalonic acid bis-[3-chlorocarbonyl-2,4,6-triiodo-5-(2,3-diacetoxy-propyl-carbamoyl)-N-methyl anilide] is dissolved in 250 ml of acetone, 5.58 g (19.5 mmol) of $Na_2CO_3 \times 10\ H_2O$, 1.89 g (18 mmol) of N-methylamino-propanediol-2,3 are added and refluxed for 2 hours. It is cooled to room temperature, the solid precipitate is suctioned off and the filtrate is evaporated in a vacuum to an oil. The oil is dissolved in 200 ml of dioxane, the remaining water is removed by azeotropic distillation and the dioxane thus consumed is replaced. 11.02 g (108 mmol) of acetic anhydride and 0.183 g (1.5 mmol) of 4-dimethylaminopyridine are added and stirred for 3 hours at 80° C. The solvent is distilled off in a vacuum, the oily residue is dissolved in ethyl acetate and chromatographed on 500 g of silica gel 60 with hexane/ethyl acetate 1:1. The corresponding fractions are collected and evaporated in a vacuum to a solid foam. The yield is 20.94 g (10.74 mmol)=71.6% of theory.

c) Hydroxymalonic acid bis-[3-(2,3-dihydroxy-N-methyl-propylcarbamoyl)-5-(2,3-dihydroxy-propylcarbamoyl)-2,4,6-triiodo-N-methyl anilide]

19.5 g (10 mmol) of bromomalonic acid bis-[3-(2,3-diacetoxy-N-methyl-propylcarbamoyl)-5-(2,3-diacetoxy-propylcarbamoyl)-2,4,6-triiodo-N-methyl anilide] is dissolved in 50 ml of DMF, 4.91 g (50 mmol) of potassium acetate is added and the solution is stirred for b 12 hours at 50° C. The reaction solution is then precipitated in 500 ml of water, and the intermediate peracetate precipitates out as amorphous precipitate. This precipitate is suctioned off, washed with water, suspended in 100 ml of water and saponified with concentrated NaOH at pH 10–12 and 50°. On completion of the saponification, it is neutralized with hydrochloric acid and desalted on ion-exchangers. The aqueous eluate is evaporated to dryness. The yield is 11.32 g (7.3 mmol)=73% of theory.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A dicarboxylic acid bis-(3,5-dicarbamoyl-2,4,6-triiodoanilide) of the formula

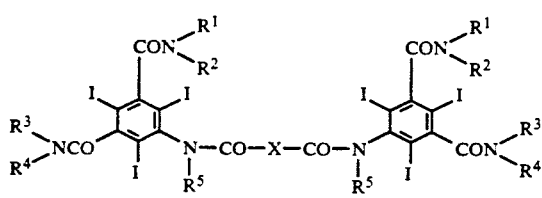

wherein the amide radicals —CONR$^1$R$^2$ and —CONR$^3$R$^4$ are different from one another and R$^1$ is hydrogen, C$_{1-4}$-alkyl or R$^2$, wherein R$^1$ and R$^2$ may be the same or different, R$^2$ is monohydroxy- or polyhydroxy-C$_{2-8}$ alkyl, R$^3$ is hydrogen, C$_{1-4}$-alkyl or R$^4$, wherein R$^3$ and R$^4$ may be the same or different, R$^4$ is monohydroxy- or polyhydroxy-C$_{2-8}$-alkyl, R$^5$ is hydrogen, C$_{1-4}$-alkyl or monohydroxy- or polyhydroxy-C$_{1-4}$-alkyl, and X is C$_{1-6}$-alkylene, optionally substituted by 1 to 6 hydroxy, C$_{1-7}$-alkoxy, benzyloxy, hydroxybenzyloxy or hydroxy-C$_{1-7}$-alkoxy groups and/or interrupted by 1-3 oxygen atoms.

2. A compound of claim 1, wherein X is —CH$_2$—.

3. A compound of claim 1, wherein X is

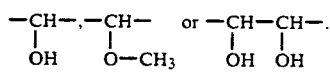

4. A compound of claim 1, wherein X is straight-chained.

5. A compound of claim 1, wherein R$^1$ is H or CH$_3$.

6. A compound of claim 1, wherein R$^2$ is

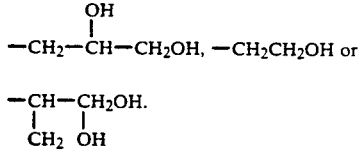

7. A compound of claim 1, wherein R$_3$ is H or —CH$_2$CH$_2$OH.

8. A compound of claim 1, wherein R$_4$ is

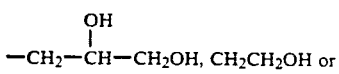

9. A compound of claim 1, wherein R$_5$ is —CH$_3$, —CH$_2$CH$_2$—OH or

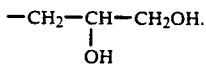

10. Malonic acid bis-[3-(2,3-dihydroxy-N-methyl-propylcarbamoyl)-5-(2,3-dihydroxy-propylcarbamoyl)-2,4,6-triiodo-N-methyl anilide], Malonic acid bis-{3-(2,3-dihydroxy-propylcarbamoyl)-5-[bis-(2-hydroxyethyl)-carbamoyl]-2,4,6-triiodo-N-methyl anilide}, Malonic acid bis-{3-(2,3-dihydroxy-propylcarbamoyl)-5-[(1RS,2SR)-2,3-dihydroxy-1-hydroxymethylpropyl-carbamoyl]-2,4,6-triiodo-N-methyl anilide}, Malonic acid bis-[3-(2-hydroxy-N-methyl-ethyl-carbamoyl)-5-(2,3-dihydroxy-propylcarbamoyl)-2,4,6-triiodo-N-(2-hydroxy-ethyl) anilide], Malonic acid bis-[3-(2,3-dihydroxy-N-methyl-propylcarbamoyl)-5-(2-hydroxy-ethyl-carbamoyl)-2,4,6-triiodo-N-methyl anilide], Malonic acid bis-{3-(2,3-dihydroxy-propylcarbamoyl)-5-(2-hydroxyethyl-carbamoyl)-2,4,6-triiodo-N-(2,3-dihydroxy-propyl) anilide}, Hydroxymalonic acid bis-[3-(2,3-dihydroxy-propylcarbamoyl)-5-(2-hydroxy-ethyl-carbamoyl)-2,4,6-triiodo-N-(2,3-dihydroxy-propyl) anilide], Hydroxymalonic acid bis-[3-(2-hydroxy-1-hydroxymethylethyl-carbamoyl)-5-(2,3-hydroxy-propyl-carbamoyl)-2,4,6-triiodo-N-methyl anilide], Methoxymalonic acid bis-[3-(2-hydroxy-1-hydroxymethylethyl-carbamoyl)-5-(2,3-dihydroxy-propyl-carbamoyl)-2,4,6-triiodo-N-methyl anilide], 2,3-dihydroxy succinic acid bis-[3-(2,3-dihydroxy-propylcarbamoyl)-5-(2-hydroxy-ethylcarbamoyl)-2,4,6-triiodo-N-(2-hydroxyethyl) anilide] or Hydroxymalonic acid bis-{3-(2,3-dihydroxy-N-methyl-propylcarbamoyl)-5-(2,3-dihydroxy-propylcarbamoyl)-2,4,6-triiodo-N-methyl anilide}, each a compound of claim 1.

11. A compound according to claim 1, wherein —CONR$^3$R$^4$ is 2,3-dihydroxypropyl-carbamoyl.

12. A compound according to claim 1, wherein —CONR$^1$R$^2$ is 2,3-dihydroxy-1-hydroxymethylpropyl-carbamoyl.

13. A compound according to claim 11, wherein —CONR$^1$R$^2$ is 2,3-dihydroxy-1-hydroxymethylpropyl-carbamoyl.

14. A compound according to claim 11, wherein X is —CH$_2$—.

15. A compound according to claim 12, wherein X is —CH$_2$—.

16. Malonic acid bis-[3-(2,3-dihydroxypropyl-carbamoyl)-5-[(1RS,2SR)-2,3-dihydroxy-1-hydroxymethylpropyl-carbamoyl]-2,4,6-triiodo-N-methyl anilide], a compound of claim 1.

17. An X-ray contrast pharmaceutical composition comprising an effective amount of a compound of claim 1 and a pharmaceutically acceptable excipient.

18. An X-ray contrast pharmaceutical composition comprising an effective amount of a compound of claim 10 and a pharmaceutically acceptable excipient.

19. A method of performing X-ray imaging of a patient comprising administering to such patient an effective amount of a compound of claim 1.

20. A method of performing X-ray imaging of a patient comprising administering to such patient an effective amount of a compound of claim 10.

* * * * *